(12) United States Patent
Brigham et al.

(10) Patent No.: US 11,040,296 B2
(45) Date of Patent: Jun. 22, 2021

(54) LIPOPHILIC DIGLYCOLAMIDE COMPOUNDS FOR EXTRACTION OF RARE EARTH METALS FROM AQUEOUS SOLUTIONS

(71) Applicant: UT-Battelle, LLC, Oak Ridge, TN (US)

(72) Inventors: Derek Brigham, Carlsbad, NM (US); Laetitia Delmau, Oak Ridge, TN (US); David DePaoli, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/407,710

(22) Filed: May 9, 2019

(65) Prior Publication Data

US 2019/0344198 A1 Nov. 14, 2019

Related U.S. Application Data

(60) Provisional application No. 62/670,013, filed on May 11, 2018.

(51) Int. Cl.
*B01D 11/02* (2006.01)
*C22B 59/00* (2006.01)
*C07C 235/04* (2006.01)

(52) U.S. Cl.
CPC ...... *B01D 11/0288* (2013.01); *B01D 11/0292* (2013.01); *C07C 235/04* (2013.01); *C22B 59/00* (2013.01); *B01D 2257/60* (2013.01)

(58) Field of Classification Search
CPC ............ B01D 11/0288; B01D 11/0292; B01D 2257/60; B01D 11/0492; B01D 11/02;
(Continued)

(56) References Cited

U.S. PATENT DOCUMENTS

| 3,821,351 A * | 6/1974 | Lucid .................... C01B 25/238 423/9 |
| 4,381,287 A * | 4/1983 | MacDonald .......... C22B 3/0012 423/70 |
| 2004/0062695 A1* | 4/2004 | Horwitz ................. B01J 20/286 423/21.5 |

(Continued)

OTHER PUBLICATIONS

Ansari S.A. et al., "Chemistry of Diglycolamides: Promising Extractants for Actinide Partitioning", Chemical Reviews, (2012), 112, pp. 1751-1772 dx.doi.org/10.1021/cr200002f.

(Continued)

*Primary Examiner* — Joseph W Drodge
(74) *Attorney, Agent, or Firm* — Scully, Scott, Murphy & Presser, P.C.

(57) ABSTRACT

A method for extracting rare earth metals (e.g., lanthanides and/or actinides) from aqueous solution, the method comprising: (i) acidifying an aqueous solution containing said rare earth metals with sulfuric acid to result in an acidified aqueous solution containing 1-12 M concentration of sulfuric acid; and (ii) contacting the acidified aqueous solution with an aqueous-insoluble hydrophobic solution comprising a rare earth extractant molecule dissolved in an aqueous-insoluble hydrophobic solvent to result in extraction of one or more of the rare earth metals into the aqueous hydrophobic solution, wherein the rare earth extractant molecule has the following structure:

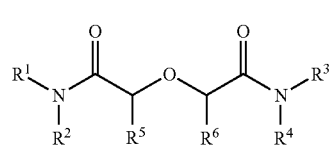

(1)

wherein $R^1$, $R^2$, $R^3$, and $R^4$ are independently selected from hydrocarbon groups containing 1-20 carbon atoms, provided that the total carbon atoms in $R^1$, $R^2$, $R^3$, and $R^4$ is at least (Continued)

12; and $R^5$ and $R^6$ are independently selected from hydrogen atom and hydrocarbon groups containing 1-3 carbon atoms.

28 Claims, 6 Drawing Sheets

(58) Field of Classification Search
CPC . B01D 11/04; B01D 11/0483; B01D 11/0488; C07C 235/04; C02F 1/26; C02F 1/44; C02F 1/62; C02F 1/66; C02F 1/68; C02F 2103/16; Y02P 10/20; C22B 59/00; C22B 3/0008; C22B 60/02; C22B 3/0005; C22B 3/0006; C22B 3/0009; C22B 3/001; C22B 3/0014; C22B 60/0217; C22B 60/0221; C22B 60/0226
USPC ....... 210/634, 638, 639, 644; 423/8, 9, 21.5, 423/54, 658.5
See application file for complete search history.

(56) References Cited

U.S. PATENT DOCUMENTS

| | | | |
|---|---|---|---|
| 2013/0259776 A1* | 10/2013 | Heres | G21F 9/125 423/9 |
| 2014/0072485 A1* | 3/2014 | Luo | G21F 9/06 423/8 |
| 2016/0346736 A1* | 12/2016 | Bhave | B01D 61/246 |

OTHER PUBLICATIONS

Gujar R.B. et al., "Development of T2EHDGA Based Process for Actinide Partitioning. Part I: Batch Studies for Process Optimization", Solvent Extraction and Ion Exchange, (2010), 28, pp. 350-366 DOI: 10.1080/07366291003685383.

Mowafy E.A. et al., "Extraction and separation of Nd(III), Sm(III), Dy(III), Fe(III), Ni(II), and Cs(I) from concentrated chloride solutions with N,N,N',N'-tetra(2-ethylhexyl) diglycolamide as new extractant", Journal of Rare Earths, (2015), 33(4), pp. 432-438 DOI: 10.1016/S1002-0721(14)60437-3.

Narbutt J. et al., "The selectivity of diglycolamide (TODGA) and bis-triazine-bipyridine (BTBP) ligands in actinide/anthanide complexation and solvent extraction separation—a theoretical approach", Dalton Transactions, (2015), 44, pp. 2567-2666 DOI: 10.1039/c4dt02657h.

Tokheim B.G., "Synthesis and characterization of new unsymmetrical diglycolamides for trivalent lanthanide metal extraction", A dissertation submitted in partial fulfillment of the requirements for the degree of Doctor of Philosophy, Washington State University, Jul. 2016, 198 pages.

Narita H. et al., "Separation of Rare Earth Elements from Base Metals in Concentrated HNO3, H2SO4 and HCl Solutions with Diglycolamide", Solvent Extraction Research and Development, Japan, (2013), 20, pp. 115-121.

* cited by examiner

LIPOPHILIC DIGLYCOLAMIDE COMPOUNDS FOR EXTRACTION OF RARE EARTH METALS FROM AQUEOUS SOLUTIONS

CROSS REFERENCE TO RELATED APPLICATION

The present application claims benefit of U.S. Provisional Application No. 62/670,013, filed on May 11, 2018, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to lipophilic compositions and their use in extracting rare earth metals (including lanthanides and/or actinides) from aqueous solutions into a hydrophobic aqueous-insoluble phase in which the lipophilic composition is dissolved.

BACKGROUND OF THE INVENTION

Rare earth element (REE) sources from industrial byproduct streams (e.g. phosphoric acid production) often contain undesired material such as uranium and thorium. The economic viability of REE recovery from such streams is significantly hampered if material needs to be removed from the product stream. This is particularly true for the radioactive elements thorium and uranium. Moreover, REEs are critical components for many modern technologies, including those of renewable energy. To increase the domestic supply of REEs, new and more effective methods for extracting REEs from industrial byproduct streams, such as those from the phosphoric acid industry, are needed. There would also be an advantage in an extraction method that can remove one or more REEs more selectively than one or more other REEs, so as to permit a separation of REEs. There would be a further advantage in such a method using straight-forward and low-cost means for extraction and separation of REEs.

SUMMARY OF THE INVENTION

In a first aspect, the present disclosure is directed to a hydrophobic liquid extraction solution useful for extracting REEs (also referred to herein as "rare earth metals") from aqueous solution. In some embodiments, the extraction solution exhibits a degree of selectivity in extracting the REEs, i.e., by extracting one or more REEs to a greater extent than one or more other REEs. The extraction solution contains a hydrophobic diglycolamide compound (rare earth extractant molecule) dissolved in an aqueous-insoluble hydrophobic solvent, such as a hydrocarbon solvent. In some embodiments, the extraction solution further includes an organoamine compound soluble in the aqueous-insoluble hydrophobic solvent, wherein the organoamine preferably contains at least one hydrocarbon group containing at least four carbon atoms. In alternative or further embodiments, the extractant solution further includes an alcohol soluble in the aqueous-insoluble hydrophobic solvent, wherein the alcohol preferably contains at least six carbon atoms.

In particular embodiments, the rare earth extractant molecule has the following structure:

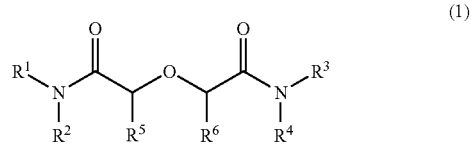

(1)

In Formula (1), $R^1$, $R^2$, $R^3$, and $R^4$ are independently selected from hydrocarbon groups containing 1-20 carbon atoms, provided that the total carbon atoms in $R^1$, $R^2$, $R^3$, and $R^4$ is at least or greater than, for example, 12, 16, 24, or 32; and $R^5$ and $R^6$ are independently selected from hydrogen atom and hydrocarbon groups containing 1-3 carbon atoms. In some embodiments, $R^1$, $R^2$, $R^3$, and $R^4$ are the same, while in other embodiments, at least one of $R^1$, $R^2$, $R^3$, and $R^4$ is different from another of $R^1$, $R^2$, $R^3$, and $R^4$.

In another aspect, the present disclosure is directed to a method for extracting rare earth metals from an aqueous solution. The method includes the following steps, at minimum: (i) acidifying an aqueous solution containing the rare earth metals with sulfuric acid to result in an acidified aqueous solution containing the rare earth metals and containing the sulfuric acid in a concentration of 1-12 M; and (ii) contacting the acidified aqueous solution with the aqueous-insoluble (hydrophobic) extractant solution described above to result in extraction of one or more of the rare earth metals into the extractant solution by binding of the rare earth extractant molecule to the one or more rare earth metals. In some embodiments, the method further includes: (iii) stripping one or more rare earth metals from the extractant solution by contacting the extractant solution with an aqueous stripping solution of sulfuric acid wherein the sulfuric acid is present in the aqueous stripping solution in a concentration of no more than 4 M, and provided that the concentration of sulfuric acid in the aqueous stripping solution is at least 0.5 M less than the concentration of sulfuric acid in the aqueous solution in step (i). Notably, the extraction process described herein is advantageously straight-forward and cost-efficient while at the same time capable of removing a substantial portion or all of the REEs from an aqueous source, and further capable of separating REEs from each other by either selective extraction, selective stripping, or both.

DETAILED DESCRIPTION OF THE INVENTION

Figure 1:
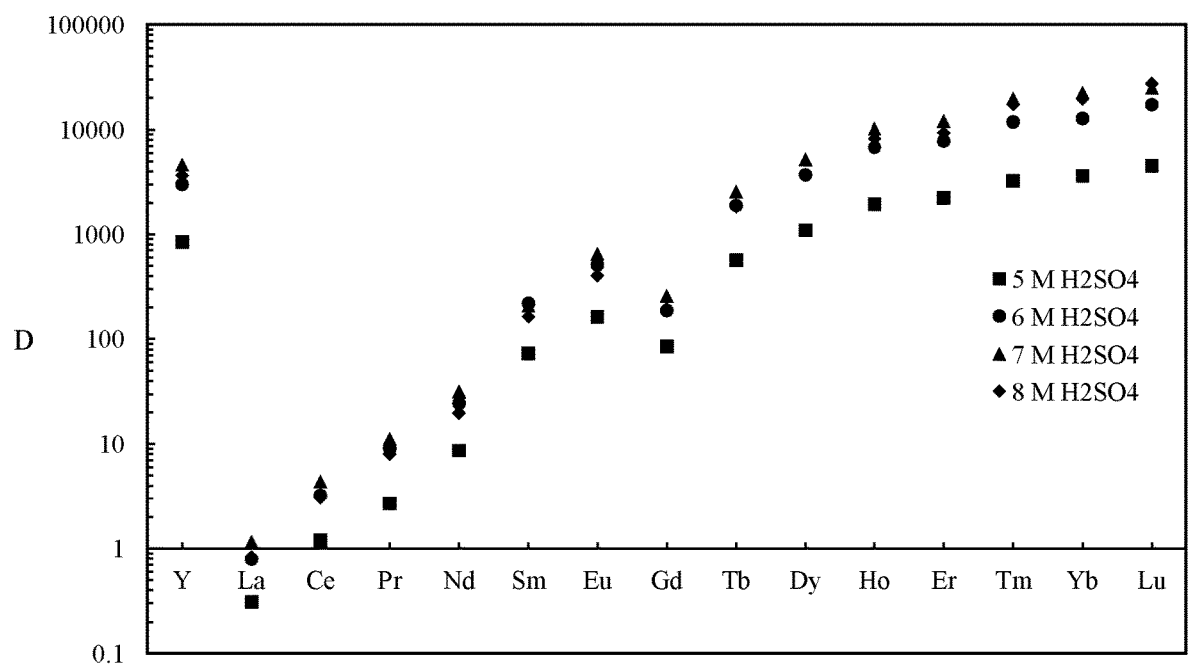
FIG. 1 is a plot showing extraction affinity (D) results for REE extraction from $H_2SO_4$ by 0.1 M TODGA 30%/vol Exxal™ 13 in Isopar-L.

As used herein, the term "hydrocarbon group" (also denoted by the group R) is defined as a chemical group composed solely of carbon and hydrogen, except that the hydrocarbon group may (i.e., optionally) be substituted with one or more fluorine atoms to result in partial or complete fluorination of the hydrocarbon group. In different embodiments, one or more of the hydrocarbon groups can contain, for example, 1, 2, 3, 4, 5, 6, 7, 8, 9, 10, 11, 12, 13, 14, 15, 16, 17, 18, 19, or 20 carbon atoms, or a number of carbon atoms within a particular range bounded by any two of the foregoing carbon numbers. Hydrocarbon groups in different compounds described herein, or in different positions of a compound, may possess the same or different number (or preferred range thereof) of carbon atoms in order to independently adjust or optimize such properties as the complexing ability, extracting (extraction affinity) ability, or selectivity of the compound.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 carbon atoms, wherein the "1-yl" suffix represents the point of attachment of the group.

In a third set of embodiments, the hydrocarbon group (R) is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 20 carbon atoms.

In a fifth set of embodiments, the hydrocarbon group (R) is unsaturated and branched, i.e., a branched olefinic or alkenyl group. Some examples of branched olefinic groups include propen-2-yl ($CH_2$=C.—$CH_3$), 1-buten-2-yl ($CH_2$=C.—$CH_2$—$CH_3$), 1-buten-3-yl ($CH_2$=CH—CH.—$CH_3$), 1-propen-2-methyl-3-yl ($CH_2$=C($CH_3$)—$CH_2$—), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 20 carbon atoms, wherein the dot in any of the foregoing groups indicates a point of attachment.

In a sixth set of embodiments, the hydrocarbon group (R) is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems.

In one aspect, the invention is directed to specialized lipophilic extractant compounds that have an ability to complex with a rare earth metal (i.e., REE) in solution and transfer (extract) the rare earth metal from an aqueous solution into an aqueous-insoluble hydrophobic (non-polar) solution in which the extractant compound is dissolved. The extractant compound contains a diglycolamide moiety and at least one, two, three, or four hydrocarbon groups that render the diglycolamide molecule soluble in a non-polar aqueous-insoluble solvent, such as a hydrocarbon solvent. The term "compound" is herein meant to be synonymous with the term "molecule".

In particular embodiments, the extractant compound has a structure within the following generic structure:

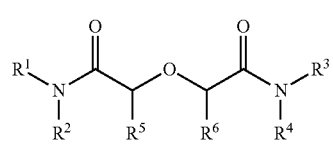

(1)

In Formula (1) above, $R^1$, $R^2$, $R^3$, and $R^4$ are independently selected from hydrocarbon groups (R) containing 1-20 carbon atoms, provided that the total carbon atoms in $R^1$, $R^2$, $R^3$ and $R^4$ (i.e., the sum of carbon atoms in all of $R^1$, $R^2$, $R^3$, and $R^4$) is at least 12. In different embodiments, the total carbon atoms in $R^1$, $R^2$, $R^3$, and $R^4$ is at least 12, 13, 14, 15, 16, 18, 20, 22, 24, 26, 28, 30, 32, 34, 36, 38, 40, 42, 44, 46, 48, 50, 52, 54, 56, 60, 64, 68, 70, 72, 76, or 80, or a total carbon number within a range bounded by any two of the foregoing values (e.g., 12-80). In some embodiments, $R^1$, $R^2$, $R^3$, and $R^4$ are the same, such as in the case where $R^1$, $R^2$, $R^3$, and $R^4$ are each n-octyl, in which case the total carbon number provided by $R^1$, $R^2$, $R^3$, and $R^4$ is 32. The term "same," as used herein, refers at least to the same carbon number in two or more of $R^1$, $R^2$, $R^3$, and $R^4$, and the term may further refer to the same structure. In other embodiments, at least one of $R^1$, $R^2$, $R^3$, and $R^4$ is different from another of $R^1$, $R^2$, $R^3$, and $R^4$, such as in the case where $R^1$ and $R^3$ are methyl groups and $R^2$ and $R^4$ are n-octyl groups, in which case the total carbon number provided by $R^1$, $R^2$, $R^3$, and $R^4$ is 18. The structure according to Formula (1) may also be symmetric or asymmetric. An example of an asymmetric structure is one in which $R^1$, $R^2$, and $R^3$ are equivalent to each other but different from $R^4$.

The groups $R^5$ and $R^6$ in Formula (1) above are independently selected from hydrogen atom and hydrocarbon groups containing 1-3 carbon atoms. In a first set of embodiments, $R^5$ and $R^6$ are hydrogen atoms. In a second set of embodiments, $R^5$ and $R^6$ are hydrocarbon groups containing 1-3 carbon atoms. In a third set of embodiments, one of $R^5$ and $R^6$ is a hydrogen atom and the other is a hydrocarbon group containing 1-3 carbon atoms. In the case where one or both of $R^5$ and $R^6$ is a hydrocarbon, the hydrocarbon is typically an alkyl group, such as a methyl, ethyl, n-propyl, or isopropyl group.

In some embodiments, $R^1$, $R^2$, $R^3$, and $R^4$ are all alkyl groups, which may be the same or different. A sub-class of Formula (1) in which $R^1$, $R^2$, $R^3$, and $R^4$ are all alkyl groups can be described by the following sub-formula:

(1a)

wherein m, n, p, and q are each independently an integer of 0-20, provided that the sum of m, n, p, and q is at least 8, and where $R^5$ and $R^6$ are as defined above. In some embodiments, m, n, p, and q are the same, such as m, n, p, and q all being 3, 4, 5, 6, 7, 8, 9, 10, 11, 12, 13, 14, 15, 16, 17, 18, or 19. In other embodiments, m, n, p, and q are not all the same, such as m and q being 0 and n and p each being 4, 5, 6, 7, 8, 9, 10, 11, 12, 13, 14, 15, 16, 17, 18, or 19; or, as another example, m and q being 1 or 2 and n and p each being 3, 4, 5, 6, 7, 8, 9, 10, 11, 12, 13, 14, 15, 16, 17, 18, or 19. Moreover, any one or more hydrogen atoms in methylene groups in Formula (Ia) may optionally be replaced with a methyl, ethyl, n-propyl, or isopropyl group, to result in a branched hydrocarbon group, provided that the branched hydrocarbon group contains up to 20 carbon atoms, as provided in Formula (1).

Some examples of specific compounds under Formula (Ia) in which all alkyl groups corresponding to $R^2$, $R^3$, and $R^4$ are the same are provided as follows:

(1a-1)

(1a-2)

(1a-3)

(1a-4)

(1a-5)

(1a-6)

(1a-7)

(1a-8)

(1a-9)

Some examples of specific compounds under Formula (Ia) in which not all alkyl groups corresponding to $R^1$, $R^2$, $R^3$, and $R^4$ are the same are provided as follows:

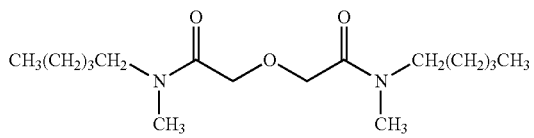

(1a-10)

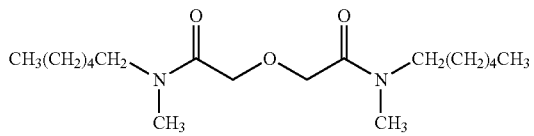

(1a-11)

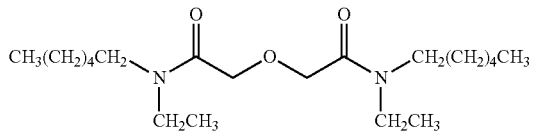

(1a-12)

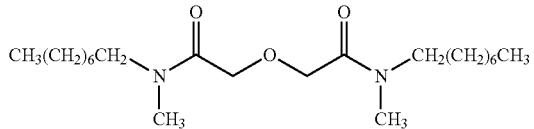

(1a-13)

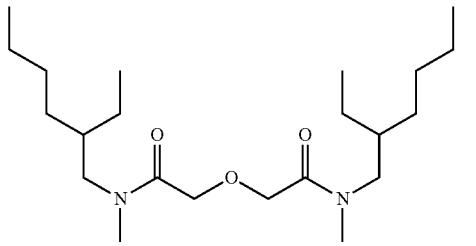

(1a-14)

The compounds according to Formula (1) and sub-formulas thereof are either commercially available or can be synthesized by methods well known in the art. Reference is made to, for example, D. D. Dicholkar et al., *Ind. Eng. Chem. Res.*, 52(7), 2457-2469, 2013, which describes the synthesis of N,N,N',N'-tetraoctyl-3-oxapentane-1,5-diamide (TODGA) in detail.

The extraction solution includes the extractant compound, described above, dissolved in an aqueous-insoluble hydrophobic solvent. The aqueous-insoluble hydrophobic solvent can be any of the hydrophobic organic solvents known in the art that are substantially or completely immiscible with water or aqueous solutions in general. The aqueous-insoluble hydrophobic solvent is typically a hydrocarbon solvent, which may be non-halogenated (e.g., hexanes, heptanes, octanes, decanes, dodecanes, benzene, toluene, xylenes, kerosene, or petroleum ether), or halogenated (e.g., methylene chloride, chloroform, carbon tetrachloride, 1,2-dichlorethane, trichloroethylene, and perchloroethylene), or etherified (e.g., diethyl ether or diisopropyl ether), or combination of halogenated and etherified (e.g., bis(chloroethyl) ether and 2-chloroethyl vinyl ether).

In some embodiments, the extractant solution, as described above, further includes an organoamine soluble in the aqueous-insoluble hydrophobic solvent. The organoamine may function to, for example, further bind to the REE, prevent formation of a third phase during the extraction, and/or assist in removing (stripping) the REE from the aqueous-insoluble hydrophobic solvent after extraction. To be soluble in the hydrophobic solvent, the organoamine should be sufficiently hydrophobic (lipophilic). To be sufficiently hydrophobic, the organoamine should contain at least one hydrocarbon group containing at least four carbon atoms. However, to ensure full solubility of the organoamine in the hydrophobic solvent, the organoamine preferably contains, in total, at least or more than six carbon atoms. In different embodiments, the organoamine may contain at least or more than, for example, 6, 7, 8, 9, 10, 11, 12, 13, 14, 15, 16, 17, 18, 19, or 20 carbon atoms, or a number of carbon atoms within a range bounded by any two of the foregoing values. The organoamine may be a primary, secondary, or tertiary amine. Some examples of primary organoamines include n-hexylamine, isohexylamine, n-heptylamine, n-octylamine, isooctylamine, n-nonylamine, n-decylamine, n-undecylamine, n-dodecylamine, n-tridecylamine, n-tetradecylamine, and n-hexadecylamine. Some examples of secondary organoamines include dibutylamine, diisobutylamine, dipentylamine, dihexylamine, diheptylamine, dioctylamine, dinonylamine, didecylamine, didodecylamine, N-methylbutylamine, N-methylpentylamine, N-methylhexylamine, N-methylheptylamine, N-methyloctylamine, N-ethylbutylamine, and N-ethyloctylamine. Some examples of tertiary organoamines include tributylamine, tripentylamine, trihexylamine, triheptylamine, trioctylamine, trinonylamine, tridecylamine, triundecylamine, and tridodecylamine.

In some embodiments, the extractant solution, as described above, further includes an organoamide soluble in the aqueous-insoluble hydrophobic solvent. The organoamide may function to, for example, further bind to the REE, prevent formation of a third phase during the extraction, and/or assist in removing (stripping) the REE from the aqueous-insoluble hydrophobic solvent after extraction. To be soluble in the hydrophobic solvent, the organoamide should be sufficiently hydrophobic (lipophilic). To be sufficiently hydrophobic, the organoamide should contain at least one hydrocarbon group containing at least four carbon atoms. However, to ensure full solubility of the organoamide in the hydrophobic solvent, the organoamide preferably contains, in total, at least or more than six carbon atoms. In different embodiments, the organoamide may contain at least or more than, for example, 6, 7, 8, 9, 10, 11, 12, 13, 14, 15, 16, 17, 18, 19, or 20 carbon atoms, or a number of carbon atoms within a range bounded by any two of the foregoing values. Some examples of hydrophobic organoamides include N-methylpentanamide, N-ethylpentanamide, N-propylpentanamide, N-butylpentanamide, N-pentylpentanamide, N-hexylpentanamide, N-methylhexanamide, N-ethylhexanamide, N-propylhexanamide, N-methyloctanamide, N-ethyloctanamide, N-propyloctanamide, N-methyldecanamide, N-ethyldecanamide, N-propyldecanamide, N,N-dimethylpentanamide, N,N-diethylpentanamide, N,N-dipropylpentanamide, N,N-dibutylpentanamide, N,N-dihexylpentanamide, and N,N-diethyloctanamide.

In some embodiments, the extractant solution, as described above, further includes an alcohol soluble in the aqueous-insoluble hydrophobic solvent. The alcohol generally functions to prevent formation of a third phase during the extraction. To be soluble in the hydrophobic solvent, the alcohol should be sufficiently hydrophobic (lipophilic). To be sufficiently hydrophobic, the alcohol should contain at least or more than six carbon atoms. In different embodiments, the alcohol contains at least or more than, for example, 6, 7, 8, 9, 10, 11, 12, 13, 14, 15, 16, 17, 18, 19, or 20 carbon atoms, or a number of carbon atoms within a range bounded by any two of the foregoing values. Some examples of lipophilic alcohols include n-hexyl alcohol, 4-methyl-1-pentanol, n-heptanol, n-octanol, 6-methyl-1-heptanol, 2-ethyl-1-hexanol, n-decanol, n-dodecanol, n-tridecanol, isotridecanol, n-tetradecanol, and n-hexadecanol.

In another aspect, the present disclosure is directed to a method for extracting one or more rare earth metals from an aqueous source solution containing the one or more rare earth metals. The term "rare earth metal," as used herein, refers to at least the lanthanide elements (elements having an atomic number of 57-71). The rare earth metals may also include scandium (Sc) and yttrium (Y). The rare earth metals may also include one or more of the actinide elements (elements having an atomic number of 90-103).

At least one lanthanide element is present in the aqueous source solution. The one or more lanthanide elements present in the aqueous source solution include one or more of the following elements: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In the aqueous source solution, the rare earth metals are present in ionic form (e.g., $Nd^{+3}$) and salt form (e.g., $Nd_2(SO_4)_3$). The aqueous source solution may also contain at least one (or one or more) of any of the actinide elements, such as uranium (U) and/or thorium (Th). In some embodiments, one or more of any of the foregoing rare earth elements are not present in the aqueous source solution.

In a first step of the extraction process (i.e., step (i)), the aqueous source solution is acidified with sulfuric acid to result in an acidified aqueous source solution containing the rare earth metals and containing the sulfuric acid in a concentration of 1-12 M. In different embodiments, the sulfuric acid concentration of the aqueous source solution is precisely or about, for example, 1, 2, 3, 4, 5, 6, 7, 8, 9, 10, 11, or 12 M, or a sulfuric acid concentration within a range bounded by any two of the foregoing values (e.g., 1-12 M, 2-12 M, 3-12 M, 1-8 M, 2-8 M, or 3-8 M), wherein the term "about" may correspond to ±50%, ±20%, or ±10% of any of the foregoing values.

In a second step of the extraction process (i.e., step (ii)), the acidified aqueous source solution from step (i) is contacted with the above-described aqueous-insoluble hydrophobic extracting solution containing a diglycolamide compound of Formula (1). The term "contacted" or "contacting," as used herein in reference to contacting of the aqueous and organic phases, generally refers to an intimate mixing of the aqueous and organic phases so as to maximize extraction of the one or more rare earth metals from the aqueous phase to the organic phase. Methods of intimately mixing liquids are well known in the art. For example, the aqueous and organic phases may be placed in a container and the container agitated. Following contact, the two phases are generally separated by means well known in the art. The foregoing described process amounts to an efficient liquid-liquid extraction process whereby one or more rare earth elements in the aqueous source solution is/are extracted, in some cases selectively, into the aqueous-insoluble hydrophobic solvent (organic phase).

The extraction process is generally capable of achieving a distribution coefficient (D), which may also herein be referred to as an extraction affinity, of at least 1 for one or more the rare earth metals, wherein D is the concentration ratio of the rare earth metal in the organic phase divided by its concentration in the aqueous phase. In some embodiments, a D value of greater than 1 is achieved, such as a D value of at least or above 2, 5, 10, 20, 50, 100, 150, 200, 250, 500, or 1000. The selectivity of the process can be characterized by the separation factor (SF), wherein SF is calculated as the ratio of D for two different ions, such as any two of the ions disclosed above, such as selectivity of an earlier lanthanide (e.g., Nd) relative to one or more later lanthanides (e.g., Tb), in which particular case $SF=D_{Nd}/D_{Tb}$. Selectivity is generally evident in an SF value greater than 1. In some embodiments, an SF value of at least or greater than 2, 5, 10, 20, 50, 100, 150, 200, 250, 500, or 1000 is achieved.

In some embodiments, the extraction step (step ii) extracts one or more rare earth elements to a greater degree (i.e., by a greater D value) than one or more other rare earth elements. By extracting one or more elements to a greater degree than one or more elements, the extraction step is exhibiting a degree in selectivity. The degree of selectivity can be adjusted by, for example, selection of the extracting molecule according to Formula (1); selection of the concentration of the extracting molecule in the hydrophobic solution; and selection of the acid concentration in the aqueous source solution. For example, depending on the foregoing conditions employed, the extraction step may extract one or more early lanthanide elements (e.g., La, Ce, Pr, and/or Nd) to a lesser extent (i.e., at a lower D value) than one or more later lanthanide elements (e.g., Sm, Eu, Gd, Tb, Dy, Ho, Er, Tm, Yb, and/or Lu) or Y. As another example, the extraction step may extract one or more lanthanide elements to a greater extent than one or more actinide elements (e.g., Th and/or U), or vice-versa.

In some embodiments, the extraction method described above further includes a successive stripping step (step (iii)). In the stripping step, one or more rare earth elements contained in the aqueous-insoluble hydrophobic solution is contacted with an aqueous stripping solution of sulfuric acid in which the sulfuric acid is present in a concentration of no more than 4 M, and provided that the concentration of sulfuric acid in the aqueous stripping solution is at least 0.5 M less (or at least 1 M, 1.5 M, 2 M, 3M, or 4M less) than the concentration of sulfuric acid in the aqueous source solution in step (i). In different embodiments, sulfuric acid concentration in the stripping solution is precisely, about, up to (no more than), or less than, for example, 4 M, 3.5 M, 3 M, 2.5 M, 2 M, 1.5 M, 1 M, 0.5 M, 0.25 M, 0.1 M, 0.05 M, 0.02 M, or 0.01 M, or a concentration within a range bounded by any two of the foregoing values (e.g., 0.01-4 M, 0.01-3 M, 0.01-2 M, 0.01-1 M, 0.01-0.5 M, 0.01-0.2 M, or 0.01-0.1M). Typically, the lower acid concentration in the stripping solution favors removal (extraction) of lighter lanthanides over heavier lanthanides and actinides (from the hydrophobic solution into the stripping solution). As an example, the aqueous source solution may be acidified to 6 M, 7 M, or 8 M, and the stripping solution may be at 5.5 M, 5 M, 4 M, 3 M, 2 M, 1 M, 0.5 M, 0.1 M, or 0.01 M acid concentration.

Examples have been set forth below for the purpose of illustration and to describe certain specific embodiments of the invention. However, the scope of this invention is not to be in any way limited by the examples set forth herein.

Examples

Using diglycolamide (DGA) based neutral extractants, a solvent system has herein been developed to extract REEs out of molar quantity solutions of sulfuric acid. The functional group of the extractant contains two amides connected via an ether bridge, with each nitrogen atom of the amides containing two substituent groups. These substituents can be a combination of different hydrocarbyl groups. The organic phase used in the following experiments contains the DGA extractant and phase modifiers of organic soluble amines and organic soluble alcohols, all of which are dissolved in a paraffinic diluent. N,N,N',N'-tetraoctyldiglycolamide (TODGA) was used in the following experiments as the DGA extractant molecule. The aqueous phase for back-extraction stripping of the metal-loaded organic phase contains millimolar quantities of sulfuric acid.

Figure 2:
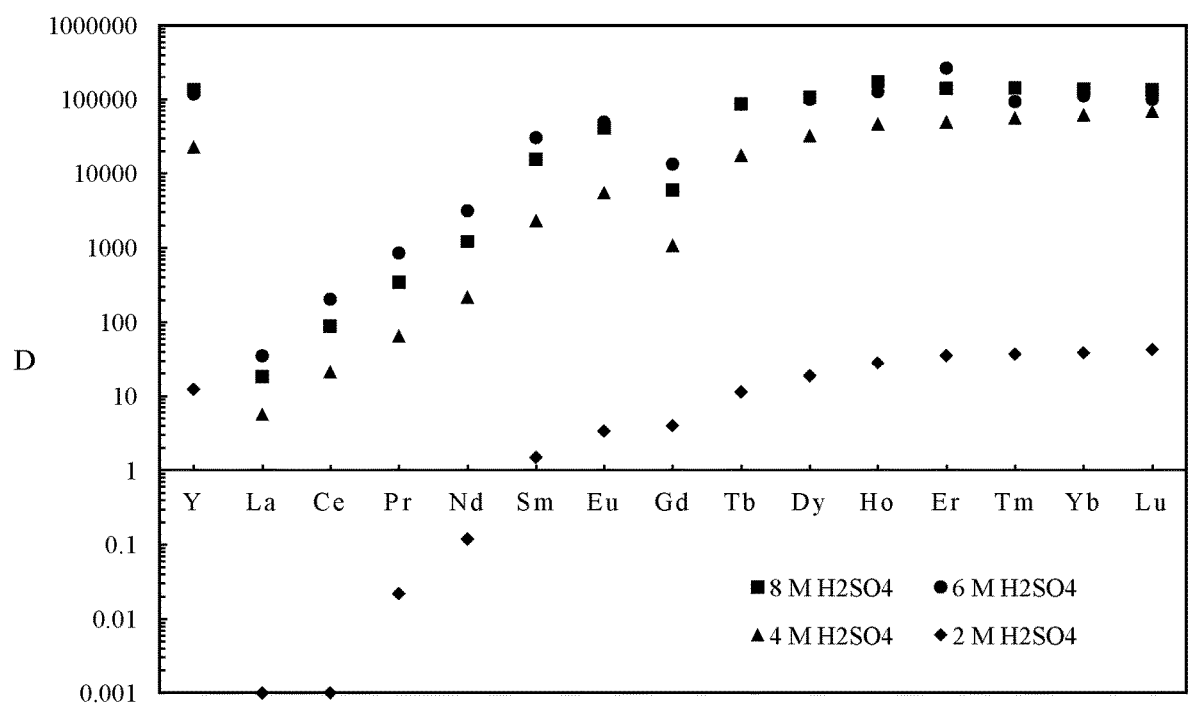
FIG. 2 is a plot showing D results for REE extraction from $H_2SO_4$ by 0.4 M TODGA+30%/vol Exxal™ 13 in Isopar-L.

FIG. 1 is a plot showing the distribution coefficients (D values) of the REEs from extraction out of various concentrations of sulfuric acid by using 0.1 M TODGA and 30 vol % Exxal™ (long chain alcohols, e.g., $C_8$-$C_{13}$ alcohols, including isotridecanol) in Isopar-L (a paraffinic diluent). FIG. 2 is a plot showing the distribution coefficients of the REEs from extraction out of various concentrations of sulfuric acid by using 0.4 M TODGA and 30 vol % Exxal™ (isotridecanol) in Isopar-L. Notably, in FIG. 2, La and Ce demonstrated little to no extraction from 2 M sulfuric acid and are ascribed D values of 0.001 as place holders. The organic solvent contains TODGA, the aliphatic alcohol Exxal™ 13, and the paraffinic diluent Isopar-L (these systems do not contain the amine modifier). The results in FIGS. 1 and 2 show that TODGA can strongly extract REEs from molar quantities of sulfuric acid. It is likely that the extraction could be achieved at lower acid concentrations with the addition of aqueous soluble bisulfate salts, such as sodium bisulfate.

Figure 3:
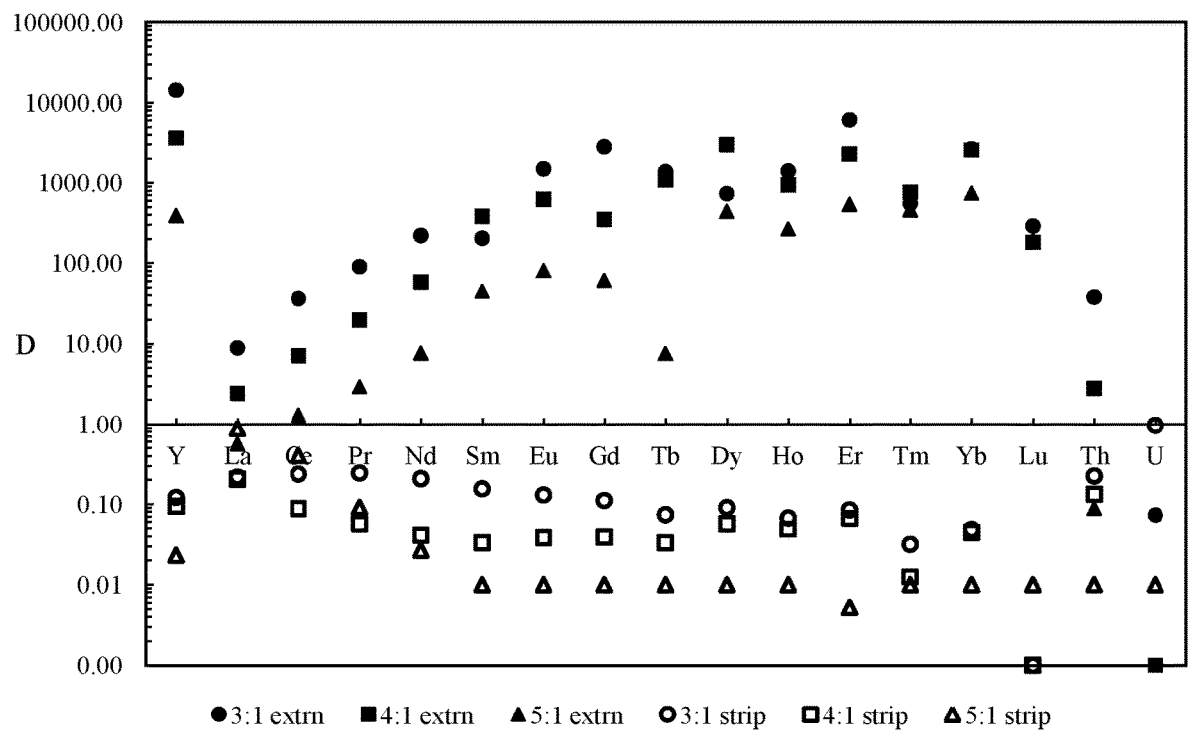
FIG. 3 is a plot showing D results for acidification ratios (leach:acid) extraction by 0.2 M TODGA+0.02 M TOA 30% v/v Exxal™ 13 in Isopar-L, and strip solution (0.01 M $H_2SO_4$). Plot shows results for 3:1, 4:1, and 5:1 acidification ratios for extraction step, and 3:1, 4:1, and 5:1 acidification ratios for stripping step.
Figure 4:
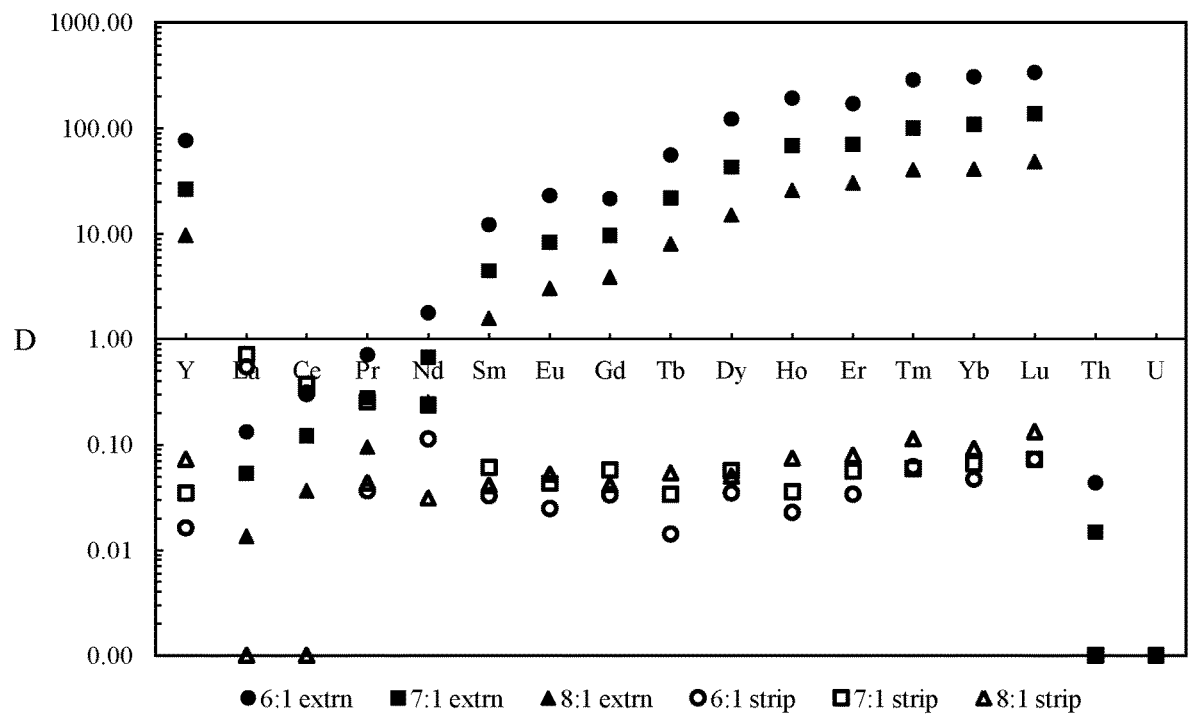
FIG. 4 is a plot showing D results for acidification ratios (leach:acid) extraction by 0.2 M TODGA+0.02 M TOA 30% v/v Exxal™ 13 in Isopar-L, and strip solution (0.01 M $H_2SO_4$). Plot shows results for 6:1, 7:1, and 8:1 acidification ratios for extraction step, and 6:1, 7:1, and 8:1 acidification ratios for stripping step.

The solvent system described here is also able to provide a separation between REE and the radioactive elements Th and U. This separation has been demonstrated using leach samples of byproduct material provided by industry. The leach is performed with a low concentration of sulfuric acid, and therefore the samples must be acidified with concentrated sulfuric acid to provide conditions conducive to extraction. FIGS. 3 and 4 contain the extraction and stripping distribution coefficients for the REEs (in this case, lanthanides), Th, and U at the different acidification ratios (parts leach to parts concentrated $H_2SO_4$). The organic solvent contains technical grade TODGA, the aliphatic amine trioctylamine (TOA), the aliphatic alcohol Exxal™ 13, and the paraffinic diluent Isopar-L. As evidenced by the data in FIGS. 3 and 4, the REE can be successfully extracted and stripped out under a large variety of initial aqueous acidity extraction conditions. The results in FIGS. 3 and 4 also show that the aqueous extraction conditions can be tuned to give stronger REE (lanthanide) extraction by increasing the acid concentration, or provide a greater separation of the REE (lanthanide) from Th and U by decreasing the acid concentration. The extraction results provided in FIGS. 1-4 indicate that selective stripping of a loaded organic phase could be achieved by first extracting at a high sulfuric acid or bisulfate salt concentration, and then back-extracting at lower acid or bisulfate concentrations.

Figure 5:
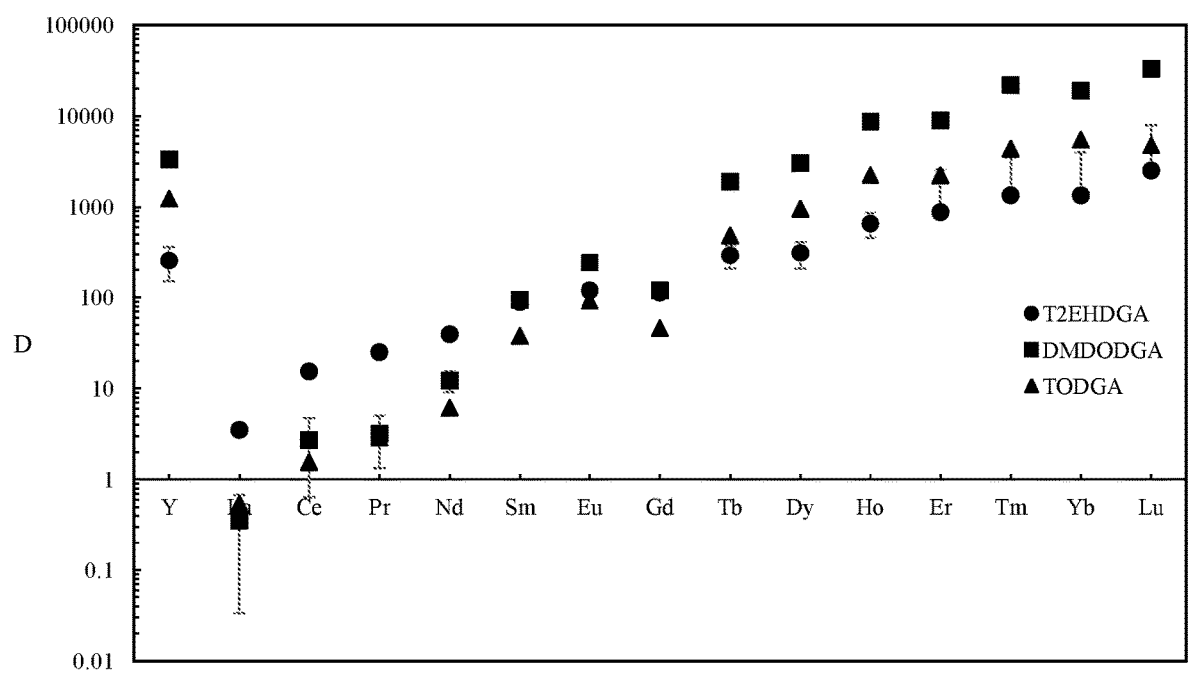
FIG. 5 is a plot showing D results for extraction by 0.1 M indicated DGA 30% v/v Exxal™ 13 in IsoparL ~1 mM REE in 8-9 M $H_2SO_4$.

Additional extractants based on diglycolamide (DGA) ligands are also useful. Use of DGA ligands other than TODGA provides additional operational flexibility in terms of REE capture and separation of U and Th from REE. FIG. 5 shows the extraction of the rare earth elements (REE) by the additional DGA ligands of N,N,N',N'-tetra-(2-ethylhexyl)diglycolamide (T2EHDGA) and N,N-dimethyl-N,N-dioctyldiglycolamide (DMDODGA) out of sulfuric acid, as well as by TODGA. While they are all effective extractants, T2EHDGA shows a greater affinity for the light lanthanides over both DMDODGA and TODGA, and DMDODGA has greater affinity for the heavy lanthanides over the other two ligands. Extraction systems can be designed to use different DGA ligands according to the desired result, such as total lanthanide extraction or higher selectivity for group lanthanide separation.

Figure 6:
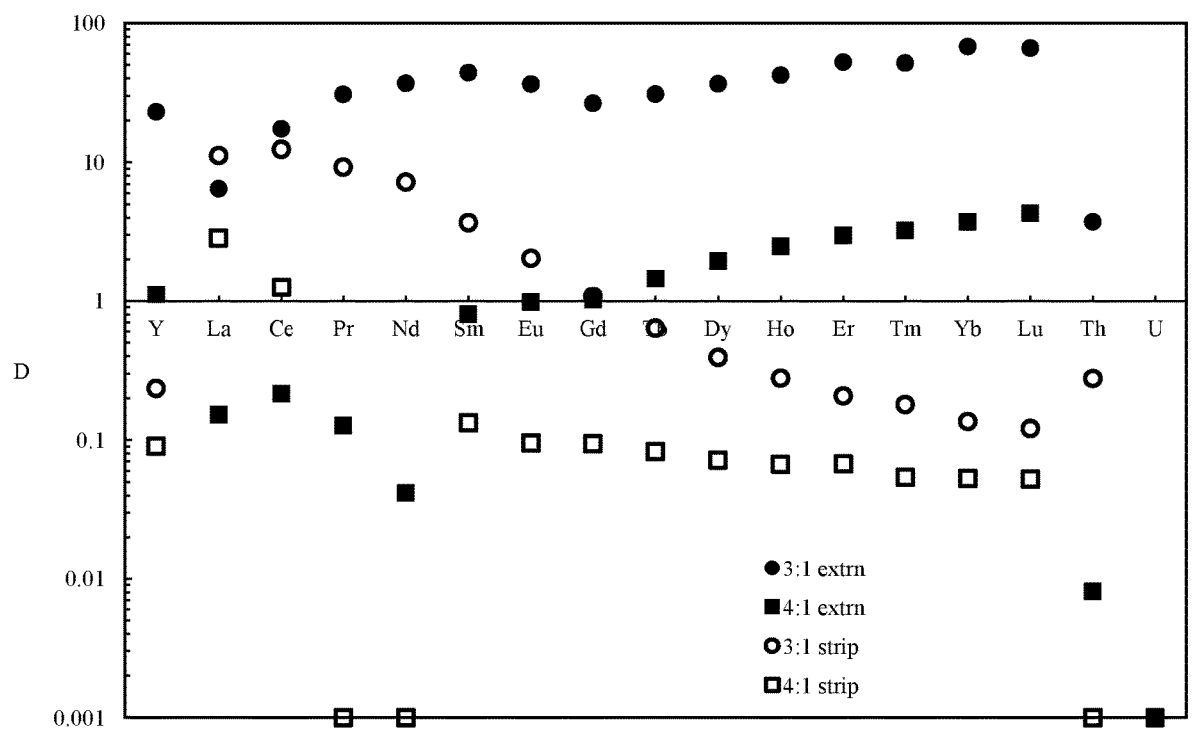
FIG. 6 is a plot showing D results for acidification ratios (leach:acid) in extraction by 0.1 M T2EHDGA 30% v/v Exxal™ 13 in IsoparL.

FIG. 6 shows the extraction and stripping results of the REE by T2EHDGA from the same type of acidified leach solutions prepared from samples provided by industry as was demonstrated for TODGA. It can be seen that, like TODGA, the T2EHDGA system has greater extraction at higher acid concentrations, and that the acid concentration can be tuned to provide a separation of the REE from thorium and uranium. This solvent system did not contain trioctylamine (TOA), and therefore, the stripping is not as effective as in the TODGA system which had TOA present. It is likely that the addition of TOA to the T2EHDGA extraction system would provide total stripping as seen in the system using TODGA with TOA.

While there have been shown and described what are at present considered the preferred embodiments of the invention, those skilled in the art may make various changes and modifications which remain within the scope of the invention defined by the appended claims.

What is claimed is:

1. A liquid solution useful for extracting rare earth metals from aqueous solutions, the liquid solution comprising a rare earth extractant molecule dissolved in an aqueous-insoluble hydrophobic solvent, wherein the rare earth extractant molecule has the following structure:

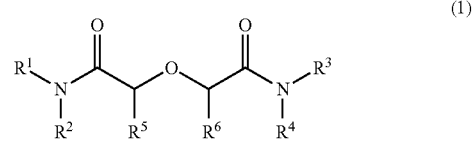

(1)

wherein $R^1$, $R^2$, $R^3$, and $R^4$ are independently selected from hydrocarbon groups containing 1-20 carbon atoms, provided that the total carbon atoms in $R^1$, $R^2$, $R^3$, and $R^4$ is at least 12; and $R^5$ and $R^6$ are independently selected from hydrogen atom and hydrocarbon groups containing 1-3 carbon atoms;

wherein the liquid solution further comprises at least one hydrophobic compound selected from the group consisting of: (i) an organoamine soluble in the aqueous-insoluble hydrophobic solvent, wherein the organoamine contains at least one hydrocarbon group containing at least four carbon atoms, and the hydrocarbon group contains solely carbon and hydrogen with optional substitution with fluorine atoms; (ii) an organoamide soluble in the aqueous-insoluble hydrophobic solvent, wherein the organoamide contains at least one hydrocarbon group containing at least four carbon atoms, and the hydrocarbon group contains solely carbon and hydrogen with optional substitution with fluorine atoms; and (iii) an alcohol soluble in the aqueous-insoluble hydrophobic solvent, wherein the alcohol contains an alkyl chain containing at least six carbon atoms.

2. The liquid solution of claim 1, provided that the total carbon atoms in $R^1$, $R^2$, $R^3$, and $R^4$ is at least 16.

3. The liquid solution of claim 1, provided that the total carbon atoms in $R^1$, $R^2$, $R^3$, and $R^4$ is at least 24.

4. The liquid solution of claim 1, provided that the total carbon atoms in $R^1$, $R^2$, $R^3$, and $R^4$ is at least 32.

5. The liquid solution of claim 1, wherein $R^1$, $R^2$, $R^3$, and $R^4$ are the same.

6. The liquid solution of claim 1, wherein at least one of $R^1$, $R^2$, $R^3$, and $R^4$ is different from another of $R^1$, $R^2$, $R^3$, and $R^4$.

7. The liquid solution of claim 1, wherein the aqueous-insoluble hydrophobic solvent is a hydrocarbon solvent.

8. The liquid solution of claim 1, wherein said at least one hydrophobic compound comprises said organoamine soluble in the aqueous-insoluble hydrophobic solvent.

9. The liquid solution of claim 1, wherein said at least one hydrophobic compound comprises said alcohol soluble in the aqueous-insoluble hydrophobic solvent.

10. The liquid solution of claim 1, wherein the organoamine is a secondary or tertiary organoamine.

11. The liquid solution of claim 1, wherein the alcohol contains at least eight carbon atoms.

12. The liquid solution of claim 1, wherein the alcohol contains at least ten carbon atoms.

13. A method for extracting rare earth metals from aqueous solution, the method comprising:
   (i) acidifying an aqueous solution containing said rare earth metals with sulfuric acid to result in an acidified aqueous solution containing said rare earth metals and containing the sulfuric acid in a concentration of 1-12 M; and
   (ii) contacting the acidified aqueous solution with an aqueous-insoluble hydrophobic solution comprising a rare earth extractant molecule dissolved in an aqueous-insoluble hydrophobic solvent to result in extraction of one or more of the rare earth metals into the aqueous-insoluble hydrophobic solution by binding of the rare earth extractant molecule to the one or more rare earth metals, wherein the rare earth extractant molecule has the following structure:

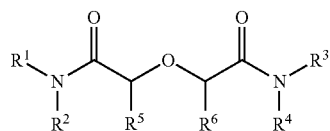

(1)

wherein $R^1$, $R^2$, $R^3$, and $R^4$ are independently selected from hydrocarbon groups containing 1-20 carbon atoms, provided that the total carbon atoms in $R^1$, $R^2$, $R^3$, and $R^4$ is at least 12; and $R^5$ and $R^6$ are independently selected from hydrogen atom and hydrocarbon groups containing 1-3 carbon atoms;

wherein the aqueous-insoluble hydrophobic solution further comprises at least one hydrophobic compound selected from the group consisting of: (i) an organoamine soluble in the aqueous-insoluble hydrophobic solvent, wherein the organoamine contains at least one hydrocarbon group containing at least four carbon atoms, and the hydrocarbon group contains solely carbon and hydrogen with optional substitution with fluorine atoms; (ii) an organoamide soluble in the aqueous-insoluble hydrophobic solvent, wherein the organoamide contains at least one hydrocarbon group containing at least four carbon atoms, and the hydrocarbon group contains solely carbon and hydrogen with optional substitution with fluorine atoms; and (iii) an alcohol soluble in the aqueous-insoluble hydrophobic solvent, wherein the alcohol contains an alkyl chain containing at least six carbon atoms;

wherein said rare earth metals are selected from lanthanides, actinides, or a combination thereof.

14. The method of claim 13, wherein the acidified aqueous solution contains the sulfuric acid in a concentration of 1-8 M.

15. The method of claim 13, wherein the acidified aqueous solution contains the sulfuric acid in a concentration of 2-8 M.

16. The method of claim 13, wherein the aqueous solution contains at least one lanthanide metal and at least one actinide metal, and the method extracts one or more lanthanide metals to a greater extent than one or more actinide metals.

17. The method of claim 16, wherein said one or more actinide metals are at least one of thorium and uranium.

18. The method of claim 13, wherein said method further comprises:
   (iii) stripping one or more rare earth metals from the aqueous-insoluble hydrophobic solution by contacting the aqueous-insoluble hydrophobic solution with an aqueous stripping solution of sulfuric acid wherein the sulfuric acid is present in the aqueous stripping solution in a concentration of no more than 4 M, and provided that the concentration of sulfuric acid in the aqueous stripping solution is at least 0.5 M less than the concentration of sulfuric acid in the aqueous solution in step (i).

19. The method of claim 18, wherein the sulfuric acid is present in the aqueous stripping solution in a concentration of no more than 1 M.

20. The method of claim 18, wherein step (iii) strips one or more lighter lanthanide elements from the aqueous-insoluble hydrophobic solution to a greater extent than one or more heavier lanthanide elements.

21. The method of claim 13, provided that the total carbon atoms in $R^1$, $R^2$, $R^3$, and $R^4$ is at least 16.

22. The method of claim 13, provided that the total carbon atoms in $R^1$, $R^2$, $R^3$, and $R^4$ is at least 24.

23. The method of claim 13, provided that the total carbon atoms in $R^1$, $R^2$, $R^3$, and $R^4$ is at least 32.

24. The method of claim 13, wherein $R^1$, $R^2$, $R^3$, and $R^4$ are the same.

25. The method of claim 13, wherein at least one of $R^1$, $R^2$, $R^3$, and $R^4$ is different from another of $R^1$, $R^2$, $R^3$, and $R^4$.

26. The method of claim 13, wherein the aqueous-insoluble hydrophobic solvent is a hydrocarbon solvent.

27. The method of claim 13, wherein said at least one hydrophobic compound comprises said organoamine soluble in the aqueous-insoluble hydrophobic solvent.

28. The method of claim 13, wherein said at least one hydrophobic compound comprises said alcohol soluble in the aqueous-insoluble hydrophobic solvent.

* * * * *